United States Patent [19]

MacGilp et al.

[11] Patent Number: 5,147,574
[45] Date of Patent: Sep. 15, 1992

[54] STABLE LIQUID SOAP PERSONAL CLEANSER

[75] Inventors: Neil A. MacGilp; Kathleen G. Baier; Richard M. Girardot; Efrain Torres, all of Cincinnati, Ohio

[73] Assignee: The Procter & Gamble Company, Cincinnati, Ohio

[21] Appl. No.: 665,620

[22] Filed: Mar. 5, 1991

[51] Int. Cl.$^5$ .......................... C11D 9/02; C11D 9/04; C11D 17/08

[52] U.S. Cl. .................................... 252/108; 252/142; 252/173; 252/DIG. 5; 252/DIG. 14

[58] Field of Search ....... 252/108, 370, 173, DIG. 14, 252/DIG. 5, 142

[56] References Cited

U.S. PATENT DOCUMENTS

| | | | |
|---|---|---|---|
| 4,190,549 | 2/1980 | Imamura et al. | 252/91 |
| 4,338,211 | 7/1982 | Stiros | 252/142 |
| 4,387,040 | 6/1983 | Straw | 252/368 |
| 4,673,525 | 6/1987 | Small et al. | 252/132 |
| 4,861,507 | 8/1989 | Gervasio | 252/108 |
| 4,917,823 | 4/1990 | Maile, Jr. | 252/548 |

FOREIGN PATENT DOCUMENTS 1235292 6/1971 United Kingdom .

OTHER PUBLICATIONS

Davidson et al.; 'Soap Manufacture,' vol. 1; p. 305; 1953.

Primary Examiner—Paul Lieberman
Assistant Examiner—E. M. Higgins
Attorney, Agent, or Firm—Leonard Williamson; Richard C. Witte

[57] ABSTRACT

The present invention relates to liquid dispersoidal cleansing compositions comprising: 55% to 90% water; 5% to 20% saturated (low IV) higher (high titer) fatty acid potassium soap; 3% to 18% of free fatty acids; said soap and said free fatty acids having a ratio of about 1:0.5 to 1:1; and wherein said liquid cleanser has a viscosity of 4,000 cps to about 100,000 cps at about 25° C.; and wherein said liquid cleanser is phase stable.

12 Claims, No Drawings

STABLE LIQUID SOAP PERSONAL CLEANSER

TECHNICAL FIELD

The present invention is related to liquid soap products, especially pumpable facial cleansers and bath/shower compositions which are formulated for viscosity control or phase stability.

BACKGROUND ART

Liquid personal cleansing compositions are well known. Patents disclosing such compositions are U.S. Pat. No. 3,697,644, Laiderman, issued Oct. 10, 1972; U.S. Pat. No. 3,932,610, Rudy et al., issued Jan. 13, 1976; U.S. Pat. No. 4,031,306, DeMartino et al., issued Jun. 21, 1977; U.S. Pat. No. 4,061,602, Oberstar et al., issued Dec. 6, 1977; U.S. Pat. No. 4,387,040, Straw, issued Jun. 7, 1983; and U.S. Pat. No. 4,917,823, Maile, Jr., issued Apr. 19, 1990; and Brit. Pat. No. 1,235,292, published Jun. 17, 1971.

More liquid soaps comprise mostly "soluble," "unsaturated," shorter chains, e.g., lauric/oleic soaps for phase stability. This, however, compromises lather quality or mildness.

Brit. Pat. 1,235,292, supra, discloses a mix of K/Na soap; at least 5% K soap; and 0.1–5% alkyl cellulose. The '292 soaps are natural. Natural fatty acids contain some unsaturation and therefore have higher Iodine Values and lower titers. The '292 exemplified liquid soaps contain from about 17% to about 21.5% soap and up to 1% free fatty acid.

U.S. Pat. No. 4,387,040, supra, discloses a stable liquid K soap containing a viscosity controlling agent composed of coco-DEA and sodium sulfate. Saturated acid soaps of $C_{12}$–$C_{14}$ are used. The viscosity of the '040 soap is 1,000–1,500 cps at 25° C., RVT/Spindle 3/10 rpm. Free fatty acid is not taught. Some of the '040 formulations contain electrolyte and polymeric thickener; but those formulations are disclosed as unstable. It should also be noted that lauric acid soap is a relatively harsh soap and when used at higher levels (as used in '040) works against product mildness.

Newtonian liquids which are too viscous are more difficult to pump than shear thinning liquids. Liquid "soap" products on the market today are mostly Newtonian or only slightly to moderately shear thinning liquids.

While it is known to use natural potassium (K) soap to make liquid cleansing compositions, there is no teaching or suggestion of solutions to certain problems encountered with superfatted, saturated, low Iodine Value (IV), higher fatty acid (FFA) soaps.

Specifically, phase stability, good lather, and viscosity control and stability are heretofore unsolved, or only partially solved, problems in this art.

While these previously disclosed liquid soap formulations are not subject, or are subject to a lesser degree, to one or more of the above-described deficiencies, it has been found that further improvements in physical stability and stability against rheological properties variations with time or temperature are desired to increase the shelf life of the product and thereby enhance consumer acceptance.

It is, therefore, an object of the present invention to provide a liquid cleansing bath/shower soap composition which is phase stable, shelf stable, lathers well, and is cosmetically attractive.

It is a further object of the present invention to provide a liquid soap cleansing composition which is relatively mild.

It is a still further object of the present invention to provide a viscous, high shear thinning liquid soap cleansing composition which is pumpable from a standard hand pressure pump container.

These and other objects of the present invention will become obvious from the detailed description which follows.

SUMMARY OF THE INVENTION

The present invention relates to a stable dispersoidal liquid soap cleansing composition comprising: 55% to 90% water; 5% to 20% saturated (low IV) higher fatty acid potassium soap; 2.5% to 18% of free fatty acids. The soap and said free fatty acids have a ratio of above about 1:0.5 to 1:1. The fatty matter, soap, and free fatty acids, have a titer (°C.) of from about 44 to about 70.

DETAILED DESCRIPTION OF THE INVENTION

The present invention relates to a stable dispersoidal liquid soap cleansing composition comprising: 55% to 90%, preferably 60% to 80%, water; 5% to 18%, preferably 6% to 14%, of mostly insoluble saturated (low IV) higher fatty acid potassium soap; 3% to 18%, preferably 4% to 9%, of free fatty acids. The soap and free fatty acids have a ratio of above about 1:0.5 to about 1:1 and preferably from about 1:0.6 to about 1:0.8. The preferred fatty acid matter is a mixture of the following saturated fatty acids on a total fatty matter basis:

$C_{12}$ at a level of about 13.5%±5%±2%;
$C_{14}$ at a level of about 35.5%±15%±5%;
$C_{16}$ at a level of about 24%±10%±5%±3%; and
$C_{18}$ at a level of about 29%±10%±5%±3%.

The fatty acid matter of the present invention has an IV of from zero to about 15, preferably below 10, more preferably below 3; and a titer of from about 44 to about 70, preferably from about 50 to 68, more preferably from about 59 to about 65.

The liquid soap of the present invention can be made without a stabilizing ingredient. However, the liquid soap preferably contains from about 0.2% to about 5%, preferably from about 0.3% to about 3%, of a stabilizing ingredient selected from the group consisting of: polymeric thickener, electrolyte, or nonionic, and mixtures thereof; preferably from 0.1% to 2% of a thickener; 0.1% to 3% electrolyte; and 0.1% to 2% nonionic, and mixtures thereof. One ore more of these ingredients improves the stability of the liquid soap. Preferably the liquid soap contains from about 0.1% to about 2% of a thickener. Preferably the liquid soap contains from about 0.1% to about 3% electrolyte. Preferably the liquid soap contains from about 0.1% to about 2% nonionic.

The liquid soap has a viscosity of 4,000–100,000 cps, preferably 10,000 cps to about 80,000 cps at about 25° C., Brook field RVTDV-II/Spindle TD/5 rpm. The preferred composition has a viscosity of 15,000–45,000 cps and, more preferably, a viscosity of 20,000–40,000 cps.

The liquid soap is called a dispersoid because at least some of the fatty matter at the levels used herein is insoluble. The level of water in the compositions is typically from about 55% to about 90%, preferably from about 60% to about 80%.

The chemical properties of some preferred pure saturated acids which have Iodine Values of zero are set out below in the Pure Acid Table.

| Pure Acid Table | | | | |
|---|---|---|---|---|
| Acid | Chain Length | Acid Value | Molecular Weight | Titer °C. |
| Decanoic | C-10 | 326 | 172 | |
| Lauric | C-12 | 280 | 200 | 44.2 |
| Myristic | C-14 | 246 | 228 | 54.4 |
| Pentadecanoic | C-15 | 231 | 242 | |
| Palmitic | C-16 | 219 | 256 | 62.9 |
| Margaric | C-17 | 207 | 270 | |
| Stearic | C-18 | 197 | 284 | 69.6 |
| Nonadecanoic | C-19 | 188 | 298 | |
| Arachidic | C-20 | 180 | 312 | |
| Behenic | C-22 | 165 | 340 | |

The titers of "natural" acids are outside of the selected fatty matter of the present invention.

| Palm Kernel Acid Table | | |
|---|---|---|
| Acid | Chain Length | Wt. % |
| Saturated: | | |
| Octanoic | C-8 | 3 |
| Decanoic | C-10 | 3 |
| Lauric | C-12 | 50 |
| Myristic | C-14 | 18 |
| Palmitic | C-16 | 8 |
| Stearic | C-18 | 2 |
| Unsaturated: | | |
| Oleic | C-18 = 1 | 14 |
| Linoleic | C-18 = 2 | 2 |
| Iodine Value: | Low | 14 |
| | High | 23 |
| Saponification Value: | Low | 245 |
| | High | 255 |
| Titer, °C. (Fatty Acid): | Low | 20 |
| | High | 28 |

Note that the titer is low.

| Coconut Acid Table | | |
|---|---|---|
| Acid | Chain Length | Wt. % |
| Saturated: | | |
| Octanoic | C-8 | 7 |
| Decanoic | C-10 | 6 |
| Lauric | C-12 | 50 |
| Myristic | C-14 | 18 |
| Palmitic | C-16 | 8.5 |
| Stearic | C-18 | 3 |
| Unsaturated: | | |
| Oleic | C-18 = 1 | 6 |
| Linoleic | C-18 = 2 | 1 |
| Linolenic | C-18 = 3 | 0.5 |
| Iodine Value: | Low | 7.5 |
| | High | 10.5 |
| Saponification Value: | Low | 250 |
| | High | 264 |
| Titer, °C. (Fatty Acid): | Low | 20 |
| | High | 24 |

The Iodine Value of coconut acid is acceptable, but its titer is low.

| Tallow BFT Table | | |
|---|---|---|
| Acid | Chain Length | Wt. % |
| Saturated: | | |
| Myristic | C-14 | 3 |
| Pentadecanoic | C-15 | 0.5 |
| Palmitic | C-16 | 24 |
| Margaric | C-17 | 1.5 |
| Stearic | C-18 | 20 |
| Unsaturated: | | |
| Myristoleic | C-14 = 1 | 1 |
| Palmitoleic | C-16 = 1 | 2.5 |
| Oleic | C-18 = 1 | 43 |
| Linoleic | C-18 = 2 | 4 |
| Linolenic | C-18 = 3 | 0.5 |
| Iodine Value: | Low | 45 |
| | High | 50 |
| Saponification Value: | Low | 192 |
| | High | 202 |
| Titer, °C. (Fatty Acid): | Low | 40 |
| | High | 45 |

Another important attribute of the preferred liquid soap of the present invention is its pumpability, particularly after storage over a cycle of temperatures. A less preferred liquid product is one in which its initial viscosity is pumpable, but there is an unacceptable increase in its viscosity which makes it unpumpable after heating to a temperature of 45° C. for about 8 hours and cooling to room temperature. The more preferred liquid soaps of the present invention can withstand more than one such cycle.

The term "pumpable" as used herein means that the liquid soap can be pumped from a standard glass or plastic container having a hand pressure actuated pump on the order of a commercially available one sold by Calmar Co., Cincinnati, Ohio, under the trade name of Dispenser SD 200, with a delivery of about 1.7 cc of the liquid soap. Another standard pump is sold by Specialty Packaging Products, Bridgeport, Conn., under the trade name LPD-2 Pump. This pump delivers about 1.7 cc of liquid.

The "shelf viscosity" of "cycle viscosity" of a liquid soap product is defined herein as its viscosity after subjection to one or more temperature cycles. This is used to describe the shelf or storage stability of liquid soaps which are formulated for use in a standard pressure actuated pump dispenser. The preferred product is formulated to provide the desired phase stability, viscosity and lather. It does not separate or become too viscous after heating and cooling under ambient conditions.

The terms "Initial Viscosity" and "Cycle Viscosity" as used herein are defined according to the methods taught herein, unless otherwise indicated. In short, the "Cycle Viscosity" is measured after the liquid soap has gone through a cycle of 49.5° C. for 8 hrs. and returned to 25° C. The term "viscosity" as used herein means both of these viscosities as measured by a Brookfield RVTDV-II/Spindle TD at 5 rpm at 25° C., unless otherwise specified.

The liquid soap product of the present invention has an Initial Viscosity of from about 10,000 cps to about 60,000 cps and/or a Cycle Viscosity of from about 15,000 cps to about 80,000 cps.

The liquid soap product of the present invention is shear thinning. Its high shear thinning factor allows it to be pumped from a standard hand pressure actuated pump, notwithstanding its relatively high viscosity of 10,000 cps to 60,000 cps.

The preferred liquid soap dispersoidal has a high shear thinning factor as defined herein. Its viscosity is reduced by at least a factor 1.5, preferably at least about 2, more preferably at least about 3. The "shear thinning factor" is:

$$\frac{\text{Viscosity at a shear rate of 1 sec}^{-1}}{\text{Viscosity at a shear rate of 10 sec}^{-1}}$$

Viscosities are measured on a Bohlin VOR Rheometer at room temperature (25° C.). Note: The following Bohlin viscosities are different from those measured on the Brookfield Viscometer.

E.g., a liquid soap (like Example 1B below) which has a Bohlin viscosity of about 38,000 cps, at a shear rate of about 1 sec$^{-1}$ and a Bohlin viscosity of about 4,000 cps at a shear rate of about 10 sec$^{-1}$. The shear thinning factor for this liquid is about 38,000/4,000 or about 9.5.

The shear thinning factors for the present invention are from about 1.5 to about 25, preferably from about 2 to about 20, more preferably from about 3 to about 15.

Additional viscosity measurements obtained with the Bohlin Rheometer show some approximate shear thinning factors for some commercially available liquid cleansers and this invention and are set out below after the Examples.

Preferably the liquid soap contains from about 0.2% up to a total of about 5%, preferably from about 0.3% to about 3%, of a stabilizing ingredient selected from the groups consisting of: from 0.1% to 2% of a thickener; 0.1% to 3% electrolyte; and 0.1% to 2% nonionic, and mixtures thereof. One or more of these ingredients can improve the stability of the liquid soap. The more dilute the liquid, the more of these stabilizing ingredients can be added.

Thickeners

The thickeners in this invention are categorized as cationic, nonionic, or anionic and are selected to provide the desired viscosities. Suitable thickeners are listed in the Glossary and Chapters 3, 4, 12 and 13 of the *Handbook of Water-Soluble Gums and Resins*, Robert L. Davidson, McGraw-Hill Book Co., New York, N.Y., 1980, incorporated by reference herein.

The liquid personal cleansing products can be thickened by using polymeric additives that hydrate, swell or molecularly associate to provide body (e.g., hydroxypropyl guar gum is used as a thickening aid in shampoo compositions).

The nonionic cellulosic thickeners include, but are not limited to, the following polymers:
1. hydroxyethyl cellulose;
2. hydroxymethyl cellulose;
3. hydroxypropyl cellulose; and
4. hydroxybutyl methyl cellulose.

The anionic cellulosic thickener includes carboxymethyl cellulose and the like.

The preferred thickener is xanthan gum having a molecular weight (M.W.) of from about 2,000,000±500,000. Each molecule has about 2,000 repeating units.

Another preferred thickener is acrylated steareth-20 methylacrylate copolymer sold as Acrysol ICS-1 by Rohm and Haas Company.

The amount of polymeric thickener found useful in the present compositions is about 0.1% to about 2%, preferably from about 0.2% to about 1.0%.

Electrolyte

An additional requirement for the present compositions is that they contain a low level of electrolyte. Electrolytes include inorganic salts (e.g., potassium or sodium chloride), as well as organic salts (e.g., sodium citrate, potassium acetate). Potassium chloride is preferred. The amount of electrolyte varies with the type of surfactant system but should be present in finished product at a level of from about 0.1% to about 3%, preferably from about 0.25% to about 2.9%. In addition to the above-mentioned chloride and citrate salts, other salts include phosphate, sulfates and other halogen ion salts. The counter ions of such salts can be sodium or other monovalent cations as well as di- and trivalent cations. It is recognized that these salts may cause instability if present at greater levels.

Nonionic Stabilizer

Another preferred component of the present invention is a nonionic. The preferred nonionic is polyglycerol ester (PGE).

Groups of substances which are particularly suitable for use as nonionic surfactants are alkoxylated fatty alcohols or alkylphenols, preferably alkoxylated with ethylene oxide or mixtures of ethylene oxide or propylene oxide; polyglycol esters of fatty acids or fatty acid amides; ethylene oxide/propylene oxide block polymers; glycerol esters and polyglycerol esters; sorbitol and sorbitan esters; polyglycol esters of glycerol; ethoxylated lanolin derivatives; and alkanolamides and sucrose esters.

Optional Components

If present, the optional components individually generally comprise from about 0.001% to about 10% by weight of the composition.

The liquid cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; and thickeners and viscosity modifiers such as $C_8$–$C_{18}$ ethanolamide (e.g., coconut ethanolamide) and polyvinyl alcohol; skin moisturizers such as glycerine; pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate.

Surfactant

An important attribute of the preferred liquid soap personal cleansing product of the present invention is its rich and creamy lather.

The preferred compositions also contains from about 1% to about 10%, preferably from about 2% to about 6%, of a high lathering synthetic surfactant.

An important optional component of the present compositions is a lather boosting surfactant. The surfactant, which may be selected from any of a wide variety of anionic (nonsoap), amphoteric, zwitterionic, nonionic and, in certain instances, cationic surfactants, is present at a level of from about 1% to about 10%, preferably from about 2% to about 6% by weight of the liquid product.

The cleansing product patent literature is full of synthetic surfactant disclosures. Some preferred surfactants as well as other cleansing product ingredients are disclosed in the following references:

| Pat. No. | Issue Date | Inventor(s) |
| --- | --- | --- |
| 4,061,602 | 12/1977 | Oberstar et al. |
| 4,234,464 | 11/1980 | Morshauser |
| 4,472,297 | 9/1984 | Bolich et al. |
| 4,491,539 | 1/1985 | Hoskins et al. |
| 4,540,507 | 9/1985 | Grollier |
| 4,565,647 | 1/1986 | Llenado |
| 4,673,525 | 6/1987 | Small et al. |
| 4,704,224 | 11/1987 | Saud |
| 4,788,006 | 11/1988 | Bolich, Jr., et al. |
| 4,812,253 | 3/1989 | Small et al. |
| 4,820,447 | 4/1989 | Medcalf et al. |
| 4,906,459 | 3/1990 | Cobb et al. |
| 4,923,635 | 5/1990 | Simion et al. |
| 4,954,282 | 9/1990 | Rys et al. |

All of said patents are incorporated herein by reference. A preferred synthetic surfactant is shown the Examples herein. Preferred synthetic surfactant systems are selectively designed for appearance, stability, lather, cleansing and mildness.

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radio-labeled water ($^3H$-$H_2O$) which passes from the test solution through the skin epidermis into the physiological buffer contained in the diffusate chamber. This test is described by T. J. Franz in the *J. Invest. Dermatol.*, 1975, 64, pp. 190-195; and in U.S. Pat. No. 4,673,525, Small et al., issued Jun. 16, 1987, incorporated herein by reference, and which disclose a mild alkyl glyceryl ether sulfonate (AGS) surfactant bases synbar comprising a "standard" alkyl glyceryl ether sulfonate mixture. Barrier destruction testing is used to select mild surfactants. Some preferred mild synthetic surfactants are disclosed in the above Small et al. patents and Rys et al.

Some examples of good lather-enhancing, mild detergent surfactants are e.g., sodium lauroyl sarcosinate, alkyl glyceryl ether sulfonate, sulfonated fatty esters, and sulfonated fatty acids.

Numerous examples of other surfactants are disclosed in the patents incorporated herein by reference. They include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates.

Alkyl chains for these surfactants are $C_8$-$C_{22}$, preferably $C_{10}$-$C_{18}$, more preferably $C_{12}$-$C_{14}$. Alkyl glycosides and methyl glucose esters are preferred mild nonionics which may be mixed with other mild anionic or amphoteric surfactants in the compositions of this invention. Alkyl polyglycoside detergents are useful lather enhancers. The alkyl group can vary from about 8 to about 22 and the glycoside units per molecule can vary from about 1.1 to about 5 to provide an appropriate balance between the hydrophilic and hydrophobic portions of the molecule. Combinations of $C_8$-$C_{18}$, preferably $C_{12}$-$C_{16}$, alkyl polyglycosides with average degrees of glycosidation ranging from about 1.1 to about 2.7, preferably from about 1.2 to about 2.5, are preferred.

Anionic nonsoap surfactants can be exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$-$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

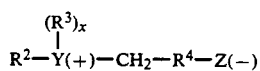

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio[-3-hydroxypentane-1-sulfate; 3-[P,P-P-diethyl-P-3,6,9-trioxatetradexocylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]butane-1-carboxylate; 3-[S-ethyl-S-(3-dodecoxy-2-hydroxypropyl)sulfonio]-propane-1-phosphonate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Niranol" and described in U.S. Pat. No. 2,528,378. Other amphoterics such as betaines are also useful in the present composition.

Examples of betaines useful herein include the high alkyl betaines such as coco dimethyl carboxymethyl betaines, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl bis-(2-hydroxyethyl) sulfopropyl betaine, amido betaines amidosulfobetaines, and the like.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

Many additional nonsoap surfactants are described in McCUTCEON'S, DETERGENTS AND EMULSIFIERS, 1979 ANNUAL, published by Allured Publishing Corporation, which is incorporated here by reference.

The above-mentioned surfactants can be used in the liquid cleansing bath/shower compositions of the present invention. The anionic surfactants, particularly the alkyl sulfates, the ethoxylated alkyl sulfates and mixtures thereof are preferred. More preferred are $C_{12}-C_{14}$ alkyl anionic surfactants selected from the group consisting of sodium alkyl glycerol ether sulfonate, sodium lauroyl sarcosinate, sodium alkyl sulfate, sodium ethoxy (3) alkyl sulfate, and mixtures thereof.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyltetradecylamine oxide, 3,6,9-trioxaheptadecyldiethylamime oxide, di(2-hydroxyethyl) tetradecylamine oxide 2-dodecoxyethyldimethylamine oxide, 3-dodecoxy-2-hydroxypropoyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:

dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethylpropylphosphine oxide, oleyldiethylphosphine oxide, dodecyldiethylphosphine oxide, tetradecyldiethylphosphine oxide, dodecyldiprophylphosphine oxide, dodecyldi(hydoxymethyl)phosphine oxide, dodecyldi(2-hydroxyethyl)phosphine oxide, tetradecylmethyl-2-hydroxypropylphosine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbons atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecyl methyl sulfoxide, 3-hydroxytridecyl methyl sulfoxide, 3-hydroxy-4-dodecosybutyl methyl sulfoxide.

The pH of the liquid cleansing bath/shower compositions herein is generally from about 8 to about 9.5, preferably from about 8.5 to about 9 as measured in a 10% aqueous solution at 25° C.

Method of Manufacture

The liquid soap cleansing compositions of the present invention may be made using techniques shown in the Examples. The preferred method for making the stable liquid comprises: (1) heating an aqueous (35–45% water) mixture of the soap:FFA to obtain a phase stable (liquid crystal) melt; (2) cooling the melt to room temperature to obtain a phase stable cream; and (3) diluting the cream with water to provide the stable dispersoidal liquid soap. These steps are preferably conducted under vacuum, but vacuum is not essential. Vacuum can be replaced with other deaeration methods, e.g., centrifugation. The dilution water preferably contains 0.5% PGE, 0.5% electrolyte, and 0.2% polymeric thickener to improve shelf stability. The preferred liquid soap has a shelf stable viscosity of from about 10,000 to about 80,000 cps (RVTDV-II, Spindle TD, 5 rpm). A viscosity of 30,000 cps (±10,000 cps) is ideal for dispensing this (high shear thinning) liquid from a standard piston-actuated displacement pump for personal cleansing. The preferred liquid soap can be formulated to be very mild by using a low soap concentration and selected higher saturated fatty acid soap chains. When a foam boosting surfactant, e.g., sarcosinate (2.5%), is added, the preferred liquid soap has very good lather.

The liquid soap cleansing compositions are useful as a cleansing aid for the entire body. The basic invention may also be applicable in other liquid type products such as liquid hand soaps.

The following methods are used to evaluate liquid soap compositions:

Method I—Initial Viscosity (100% Product)

Apparatus:
Brookfield RVTDV-II Viscometer, Helipath, Spindle TD, 4 oz. Sample Jar Conditions:
Sample Temperature Equilibrated to Room Temperature (23° C./72°–77° F.), Brookfield at 5 rpm.

Method:
Transfer approximately 120 ml of product into 4 oz. sample jar taking care not to entrain air. Allow to equilibrate at room temperature for at least 4 hrs. Calibrate and zero viscometer referring to Brookfield manual. With TD spindle installed, viscometer at 5 rpm, and helipath stand energized (downward direction), lower viscometer until spindle is nearly touching product surface. Observe as helipath moves spindle through product surface and, as soon as spindle is submerged, begin timing. After 30 seconds record the next five viscosity readings. Average these readings and record. If the viscosity of the liquid soap is from about 10,000 to about 60,000 cps, it passes this test.

Method II—Viscosity Cycle (100% Product)

Apparatus:
Brookfield RVTDV-II Viscometer, Helipath, Spindle TD, 4 oz. Sample Jar, 120° F. (~49.5° C.) Constant Temperature Room or Water Bath.

Conditions:
Cycle sample from room temperature (RT) to 49.5° C. and return to room temperature. Sample residence time at 49.5° C. must be at least 8 hrs. and when returned to RT residence time must be at least 8 hrs. before viscosity is measured. Brookfield at 5 rpm.

Method:
Transfer approximately 120 ml of product into 4 oz. sample jar taking care not to entrain air. Place sample in constant temperature 49.5° C. room, oven or water bath. Maintain product at this temperature for at least 8 hrs. Transfer product to RT and allow to equilibrate for at least 8 hrs. Calibrate and zero viscometer referring to Brookfield manual. With TD spindle installed, viscometer at 5 rpm, and helipath stand energized (downward direction), lower viscometer until spindle is nearly touching product surface. Observe as helipath moves spindle through product surface and, as soon as spindle is submerged, time for 30 seconds and then record the next five viscosity readings. Average these readings and record. If the viscosity of the liquid soap is 10,000 to 60,000 cps, it passes this test for a more preferred liquid.

Method III—Accelerated Stability

Apparatus:
Centrifuge with temperature control capability or constant temperature room, 25–30 ml Flint Glass Vial.

Conditions:
Centrifuge samples at approximately 350 g's and 120° F. (49.5° C.).

Method:
Transfer approximately 25 ml of product into glass vial taking care not to entrap air. Place sample in 49.5° C. atmosphere for at least 2 hrs. to equilibrate. Place vial into centrifuge with atmosphere controlled at 49.5° C. Centrifuge at approximately 350 g's (350×force of gravity) 1200 rpm for 4 hrs. Remove from centrifuge and observe, note product separation, if any, and record result. If a liquid soap passes this test, it is highly preferred.

EXAMPLES

The following examples further describe and demonstrate the preferred embodiments within the scope of the present invention. The Examples are given solely for the purpose of illustration and are not to be construed as limitations of the present invention as many variations thereof are possible without departing from its spirit and scope. Unless otherwise indicated, all percentages and ratios herein are approximations and by weight.

The following Example 1B is a preferred dispersoidal liquid soap of the present invention.

The Brookfield viscosity of 1B is about 30,000 cps. The Iodine Value of the fatty acids of Example 1 is about zero and its titer is about 59° C. Example 1B has totals of about 10.2% soap and 6.85% free fatty acid and 2.4% sarcosinate. The soap to free fatty acid (FFA) ratio is about 1:0.67.

TABLE 1

| | EXAMPLE 1 | |
|---|---|---|
| Formula | 1A | 1B |
| Ingredients | Wt. % | Wt. % |
| Stearic Acid | 7.55 | 4.53 |
| Palmitic Acid | 6.23 | 3.74 |
| Myristic Acid | 8.72 | 5.23 |
| Lauric Acid | 3.52 | 2.11 |
| Triclosan | 0.30 | 0.18 |
| KOH (87%) | 3.86 | 2.32 |
| Glycerine | 15.00 | 9.00 |
| Mayoquest (45%)* | 0.44 | 0.26 |
| Sodium Lauroyl Sarcosinate (30%) | 13.33 | 8.00 |
| JR-400 | 0.50 | 0.30 |
| Aloe Vera Powder | 0.01 | 0.01 |
| Perfume | 0.30 | 0.18 |
| Total Water (approx.) | 50.00 | 70.00 |

*Mayoquest is a 50/50 mixture of HEDP/DPTA

A liquid soap (Example 1B) is made by first mixing the ingredients of "1A" as follows:

1. Mix and melt all of the fatty acids with the Triclosan into a jacketed vessel and heat to 80° C.
2. Dissolve the KOH pellets with water to make a 38% solution by weight.
3. Mix the glycerine, sodium lauroyl sarcosinate, JR-400, Mayoquest, and water in a separate jacketed vessel and heat to 80° C.
4. Transfer the melted fatty acid mix of Step 1 into a vacuum vessel which contains an internal homogenizer, wall scrapers and paddle mixers. E.g., a Mizuko Brand Automatic Driving Type Vacuum Emulsifier, Model APVA-3DP, sold by Mizuko Industrial Co., Ltd., or a T. K. AGI Homo Mixer Hodel 2M-2, made by Tokushu Keka Kogyo Co., Ltd. While vacuum is not essential, it is highly preferred so that the intermediate product has a specific gravity of about 1±0.05.
5. Slowly add the KOH solution under vacuum of about 400 mm Hg while mixing and homogenizing during saponifying. Maintain temperature controlled to 80±5° C. while mixing.
6. After the saponification is complete, add the water mix of Step 3 under vacuum while continuing mixing and homogenizing. Maintain temperature controlled to 80±5° C. while mixing to obtain a phase stable melt.
7. Immediately begin cooling from 80° C. to 50° C. at a 3° C./minute rate. Maintain mixing and vacuum during cooling step but stop homogenizing.
8. Dissolve the aloe vera powder in water and add at 50° C.
9. Cool from 50° C. to 35° C. at a 0.5° C./minute rate under vacuum and while mixing.
10. At 35° stop the vacuum and add the perfume. Continue cooling with mixing until final mix reaches about 30° C. At 30° C., stop cooling and unload the mix from the vessel.
11. The cooled melt of Step 10 (1A) is then diluted with distilled water at about room temperature. The water and the cooled melt is first mixed gently to provide a uniform slurry and then transferred to the vacuum vessel of Step 4 and homogenized for about 10 minutes under about 600 mm Hg to provide an aqueous (70% water) liquid soap dispersoidal (Example 1B).

The liquid soaps can be made by varying this method, but simple mixing of the ingredients of Example 1B will not result in a stable liquid disperoid.

TABLE 2

EXAMPLES 2-6

Examples 2-6 are liquids made using the method of Example 1 except that the following stabilizing ingredients (finished liquid soap percent) are added to the dilution water of Step 11:

| KCl | 0.5% |
|---|---|
| PGE | 0.5% |
| Xanthan | 0.2% |

| | Examples 2-5 and Comparative Example 6 | | | | |
|---|---|---|---|---|---|
| | 2 | 3 | 4 | 5 | 6 |
| Ingredients | Wt. % | Wt. % | Wt. % | Wt. % | Wt. % |
| Soap | 10.2 | 5.0 | 5.0 | 20.0 | 20.0 |
| FFA | 6.8 | 5.0 | 2.5 | 10.0 | 20.0 |
| Water | 81.8 | 88.8 | 91.3 | 68.8 | 58.8 |
| Total | 100.0 | 100.0 | 100.0 | 100.0 | 100.0 |
| Soap:FFA | 1:0.66 | 1:1 | 1:0.5 | 1:0.5 | 1:1 |

In short, Examples 2-6 are prepared in the following manner:

1. heating an aqueous (~50% water) mixture of the soap:FFA to obtain a phase stable melt (Step 6 above);
2. cooling the melt to about room temperature; and
3. diluting the cooled melt with water to provide a liquid soap.

The dilution water of (3) contains the KCl, PGE and xanthan gum. The preferred liquid soap Example 2 has a Brookfield viscosity of 28,000 cps. Example 2 has a high shear thinning value and is ideal for dispensing from a standard piston actuated pump for personal cleansing. Example 2 is relatively mild due to its low soap concentration and higher chain saturated soap content. The IV is less than 1 and the titer is about 59.5 for the fatty matter used in Examples 2-6. The fatty matter of the liquid soaps used in Examples 2-6 are $C_{12}$ at 13% ±2%; $C_{14}$ at 35% ±5%; $C_{16}$ at 24%±3%; and $C_{18}$ at 29%±3% on a total fatty matter basis.

Examples 2-5 are stable liquid disperoids under normal conditions. Examples 4 and 5 separate under stress conditions defined hereinbelow as the Accelerated Stability Method III.

However, Examples 4 and 5 can be made more stable by increasing the levels of the stabilizing ingredients and/or by increasing the titer to over 60. Comparative Experimental Example 6 gels. Examples 2 and 3 are phase stable and shelf stable. Example 2 is preferred over Example 3 for better lather. The preferred liquid soap, e.g., Example 2, has a very rich creamy lather. However, in some of the following Examples, a foam-boosting surfactant, sarcosinate (2.4%), is added to enhance the rich and creamy lather.

In the following Examples 7-24, the ingredients shown as trade names are:
Mayoquest is a 50/50 mixture of HEDP/DPTA.
Triclosan is an antimicrobial.
JR-400 is polyquatermiun 10.
Capmul 8210 is mono/diglycerides of caprylic/capric acids (M.W. 250).
Caprol ET is mixed polyglycerol esters $C_{12}$-$C_{18}$ (M.W. 2300).
Caprol 10G-4-0 is decaglycerol tetraoleate (M.W. 1800).
Acrysol ICS is polymeric thickener defined above.

TABLE 3

| | EXAMPLES 7 AND 8 | |
|---|---|---|
| Ingredients | 7 Wt. % | 8 Wt. % |
| Stearic Acid | 4.53 | 4.53 |
| Palmitic Acid | 3.74 | 3.74 |
| Myristic Acid | 5.23 | 5.23 |
| Lauric Acid | 2.11 | 2.11 |
| Triclosan | 0.18 | 0.18 |
| KOH (87%) | 2.32 | 2.32 |
| Glycerine | 9.00 | 9.00 |
| Mayoquest (45%) | 0.26 | 0.26 |
| Sodium Lauroyl Sarcosinate (30%) | 8.00 | 8.00 |
| JR-400 | 0.30 | 0.30 |
| Aloe Vera Powder | 0.01 | 0.01 |
| Perfume | 0.18 | 0.18 |
| KCl | 0.50 | — |
| K-Acetate (55%) | — | 1.20 |
| Caprol ET | 0.50 | 0.50 |
| Caprol 10G-4-0 | — | — |
| Capmul 8210 | — | — |
| Acrysol ICS | — | — |
| Hydroxy Ethyl Cellulose (HEC) | — | — |
| Xanthan (M.W. 2,000,000) | 0.20 | 0.20 |
| D.I. Water | 62.94 | 62.24 |
| Accelerated Stability | Pass | Pass |
| Initial Viscosity | 22,000 | 16,000 |
| Cycle Viscosity | 49,000 | 50,000 |

Examples 7 and 8 are two full liquid soap dispersoidal compositions with different electrolytes. Example 7, which is highly preferred, contains 0.5% KCl and 2.4% of the high lathering synthetic surfactant. Example 8 contains 1.20×0.55 or 0.66% on an active basis of K-acetate. Both have acceptable viscosities. Example 7 is most preferred.

The total soap is 10.2% and the total FFA is 6.84%. The soap/FFA ratio is 1:0.67.

The level of electrolyte, K-acetate, is established as an equal molar concentration to the level of KCl used in Example 7.

The "Accelerated Stability" (Method III) is holding the liquid soaps at 120° F. (49.5° C.) for 4 hrs. under centrifuge (1200 rpm).

The "Viscosities" are measured at about 25° C. (RT) using a Brookfield RVTDV-II with Helipath Stand and a TD Spindle at 5 rpm.

TABLE 4

| | EXAMPLES 9-11 | | |
|---|---|---|---|
| Ingredients | 9 Wt. % | 10 Wt. % | 11 Wt. % |
| Stearic Acid | 4.53 | 4.53 | 4.53 |
| Palmitic Acid | 3.74 | 3.74 | 3.74 |
| Myristic Acid | 5.23 | 5.23 | 5.23 |
| Lauric Acid | 2.11 | 2.11 | 2.11 |
| Triclosan | 0.18 | 0.18 | 0.18 |
| KOH (87%) | 2.32 | 2.32 | 2.32 |
| Glycerine | 9.00 | 9.00 | 9.00 |
| Mayoquest | 0.26 | 0.26 | 0.26 |
| Sodium Lauroyl Sarcosinate (30%) | 8.00 | 8.00 | 8.00 |
| JR-400 | 0.30 | 0.30 | 0.30 |
| Aloe Vera Powder | 0.01 | 0.01 | 0.01 |
| Perfume | 0.18 | 0.18 | 0.18 |
| KCl | 0.50 | — | — |
| K-Acetate (55%) | — | — | — |
| Caprol ET | — | — | — |
| Caprol 10G-4-0 | — | — | — |
| Capmul 8210 | 0.50 | — | — |
| Acrysol ICS | — | 0.80 | — |
| Hydroxy Ethyl Cellulose (HEC) (M.W. 350,000-400,000) | — | — | 0.80 |
| Xanthan (M.W. 2,000,000) | 0.20 | — | — |
| D.I. Water | 62.94 | 63.34 | 63.34 |
| Accelerated Stability | Pass | Slight | Slight |
| Initial Viscosity | 30,000 | 58,000 | 48,000 |
| Cycle Viscosity | 160,000 | 140,000 | 200,000 |

Example 9 contains 0.5% KCl; 0.50% Capmul 8210; and 0.20% xanthan. Examples 10 and 11 contain no KCl and, respectively, 0.80% Acrysol ICS and 0.80% HEC. The levels of water in these examples are slightly higher due to water added with KOH, sarcosinate, etc. Their initial viscosities are all acceptable for pumpable liquid soaps. The cycle viscosities are, however, too high. It failed the accelerated stability test, but is a stable dispersoidal liquid soap under normal conditions. Examples 10 and 11 separated only slightly under the accelerated stability test.

Compare Example 9 with Example 15 below. They are identical, but for the low molecular weight (250) nonionic Capmul 8210 in Example 9, which appears to have a negative effect on cycle viscosity stability. Example 12 (below) is also an identical formula. Its nonionic is Caprol ET, which has a higher molecular weight (2300) than Capmul 8210. The higher molecular weight Caprol ET appears to have a positive effect on multiple cycle viscosities.

TABLE 5

| | EXAMPLES 12-15 | | | |
|---|---|---|---|---|
| Ingredients | 12 Wt. % | 13 Wt. % | 14 Wt. % | 15 Wt. % |
| Stearic Acid | 4.53 | 4.53 | 4.53 | 4.53 |
| Palmitic Acid | 3.74 | 3.74 | 3.74 | 3.74 |
| Myristic Acid | 5.23 | 5.23 | 5.23 | 5.23 |
| Lauric Acid | 2.11 | 2.11 | 2.11 | 2.11 |
| Triclosan | 0.18 | 0.18 | 0.18 | 0.18 |
| KOH (87%) | 2.32 | 2.32 | 2.32 | 2.32 |
| Glycerine | 9.00 | 9.00 | 9.00 | 9.00 |
| Mayoquest | 0.26 | 0.26 | 0.26 | 0.26 |
| Sodium Lauroyl Sarcosinate (30%) | 8.00 | 8.00 | 8.00 | 8.00 |
| JR-400 | 0.30 | 0.30 | 0.30 | 0.30 |
| Aloe Vera Powder | 0.01 | 0.01 | 0.01 | 0.01 |
| Perfume | 0.18 | 0.18 | 0.18 | 0.18 |
| KCl | 0.50 | — | 0.50 | 0.50 |
| K-Acetate (55%) | — | — | — | — |
| Caprol ET | 0.50 | 0.50 | 0.50 | — |
| Caprol 10G-4-0 | — | — | — | — |
| Capmul 8210 | — | — | — | — |
| Acrysol ICS | — | — | — | — |
| Hydroxy Ethyl Cellulose (HEC) | — | — | — | — |
| Xanthan | 0.20 | 0.20 | — | 0.20 |
| D.I. Water | 62.94 | 63.44 | 63.14 | 63.44 |
| Accelerated Stability | Pass | Pass | Pass | Pass |
| Initial Viscosity | 22,000 | 42,000 | 46,000 | 24,000 |

TABLE 5-continued

| | EXAMPLES 12-15 | | | |
|---|---|---|---|---|
| Ingredients | 12 Wt. % | 13 Wt. % | 14 Wt. % | 15 Wt. % |
| Cycle Viscosity | 49,000 | 185,000 | 37,000 | 40,000 |

Highly preferred Examples 12, 14 and 15 all have acceptable pumpable viscosities, initial and cycle, and pass the accelerated stability test. Examples 12, 14 and 15 have acceptable cycle viscosities and contain 0.5% KCl. Note than Example 13 does not contain an electrolyte cycle viscosity stabilizer and has an unacceptably high (185,000 cps) cycle viscosity. Example 14 contains no xanthan, but has an acceptable cycle viscosity. Caprol ET is a higher molecular weight (2300) nonionic and does not destroy the cycle viscosity in contrast to the lower molecular weight nonionic as used in Example 9.

TABLE 6

| | EXAMPLES 16-18 | | |
|---|---|---|---|
| Ingredients | 16 Wt. % | 17 Wt. % | 18 Wt. % |
| Stearic Acid | 4.53 | 4.53 | 4.53 |
| Palmitic Acid | 3.74 | 3.74 | 3.74 |
| Myristic Acid | 5.23 | 5.23 | 5.23 |
| Lauric Acid | 2.11 | 2.11 | 2.11 |
| Triclosan | 0.18 | 0.18 | 0.18 |
| KOH (87%) | 2.32 | 2.32 | 2.32 |
| Glycerine | 9.00 | 9.00 | 9.00 |
| Mayoquest | 0.26 | 0.26 | 0.26 |
| Sodium Lauroyl Sarcosinate (30%) | 8.00 | 8.00 | 8.00 |
| JR-400 | 0.30 | 0.30 | 0.30 |
| Aloe Vera Powder | 0.01 | 0.01 | 0.01 |
| Perfume | 0.18 | 0.18 | 0.18 |
| KCl | 0.50 | — | — |
| K-Acetate (55%) | — | — | — |
| Caprol ET | — | — | 0.50 |
| Caprol 10G-4-0 | — | — | — |
| Capmul 8210 | — | — | — |
| Acrysol ICS | — | — | — |
| Hydroxy Ethyl Cellulose (HEC) | — | — | — |
| Xanthan | — | 0.20 | — |
| D.I. Water | 63.64 | 63.94 | 63.64 |
| Accelerated Stability | Pass | Fail | Fail |
| Initial Viscosity | 37,000 | 11,000 | 24,000 |
| Cycle Viscosity | 35,000 | 222,000 | 180,000 |

Examples 16-18 all have acceptable initial viscosities. Example 16 has acceptable properties. Like Example 13, Examples 17 and 18 do not contain an electrolyte. Example 16 has 0.50% KCl and Examples 17 and 18 do not have the viscosity stabilizing electrolyte. Examples 17 and 18 also failed the accelerated stability test, but at room temp. are phase stable liquid soaps.

TABLE 7

| | EXAMPLES 19-21 | | |
|---|---|---|---|
| Ingredients | 19 Wt. % | 20 Wt. % | 21 Wt. % |
| Stearic Acid | 4.53 | 4.53 | 4.53 |
| Palmitic Acid | 3.74 | 3.74 | 3.74 |
| Myristic Acid | 5.23 | 5.23 | 5.23 |
| Lauric Acid | 2.11 | 2.11 | 2.11 |
| Triclosan | 0.18 | 0.18 | 0.18 |
| KOH (87%) | 2.32 | 2.32 | 2.32 |
| Glycerine | 9.00 | 9.00 | 9.00 |
| Mayoquest | 0.26 | 0.26 | 0.26 |
| Sodium Lauroyl Sarcosinate (30%) | 8.00 | 8.00 | 8.00 |
| JR-400 | 0.30 | 0.30 | 0.30 |
| Aloe Vera Powder | 0.01 | 0.01 | 0.01 |
| Perfume | 0.18 | 0.18 | 0.18 |
| KCl | 0.50 | — | 0.50 |
| K-Acetate (55%) | — | 1.20 | — |
| Caprol ET | 0.50 | 0.50 | 0.50 |
| Caprol 10G-4-0 | — | — | — |
| Capmul 8210 | — | — | — |
| Acrysol ICS | — | — | — |
| Hydroxy Ethyl Cellulose (HEC) | — | — | — |
| Xanthan | 0.20 | 0.20 | — |
| D.I. Water | 62.94 | 62.24 | 63.14 |

Examples 19-21 are tested for multiple cycle viscosity stability. Their initial and multiple cycle viscosities are set out below in cps×1000.

| | 19 | 20 | 21 |
|---|---|---|---|
| Initial | 24 | 16 | 46 |
| Cycle 1 | 44 | 50 | 37 |
| Cycle 2 | 38 | 80-100 | 35-75 |
| Cycle 3 | 26 | 60 | 28-45 |
| Cycle 4 | 38 | 65 | 30-45 |
| Cycle 5 | 35-60 | — | — |

TABLE 8

| | EXAMPLES 22-24 | | |
|---|---|---|---|
| Ingredients | 22 Wt. % | 23 Wt. % | 24 Wt. % |
| Stearic Acid | 4.53 | 4.53 | 4.53 |
| Palmitic Acid | 3.74 | 3.74 | 3.74 |
| Myristic Acid | 5.23 | 5.23 | 5.23 |
| Lauric Acid | 2.11 | 2.11 | 2.11 |
| Triclosan | 0.18 | 0.18 | 0.18 |
| KOH (87%) | 2.32 | 2.32 | 2.32 |
| Glycerine | 9.00 | 9.00 | 9.00 |
| Mayoquest | 0.26 | 0.26 | 0.26 |
| Sodium Lauroyl Sarcosinate (30%) | 8.00 | 8.00 | 8.00 |
| JR-400 | 0.30 | 0.30 | 0.30 |
| Aloe Vera Powder | 0.01 | 0.01 | 0.01 |
| Perfume | 0.18 | 0.18 | 0.18 |
| KCl | 0.50 | 0.50 | 0.50 |
| K-Acetate (55%) | — | — | — |
| Caprol ET | — | — | — |
| Caprol 10G-4-0 | — | — | 0.50 |
| Capmul 8210 | — | — | — |
| Acrysol ICS | — | — | — |
| Hydroxy Ethyl Cellulose (HEC) | — | — | — |
| Xanthan | 0.20 | — | 0.20 |
| D.I. Water | 63.44 | 63.64 | 62.94 |

The multiple cycle viscosities (cps×1000) of Examples 22-24 are:

| | 22 | 23 | 24 |
|---|---|---|---|
| Initial | 24 | 6 | N/A |
| Cycle 1 | 40 | 43 | N/A |
| Cycle 2 | 60-70 | 25-50 | N/A |
| Cycle 3 | 60 | 45-75 | N/A |
| Cycle 4 | 115 | 120-180 | N/A |
| Cycle 5 | — | 75-130 | N/A |

N/A = not available.

The liquid cleansing composition preferably has an initial viscosity of from about 20,000 to about 40,000 cps and a cycle viscosity of from about 25,000 cps to about 70,000 cps.

A series of Examples are made to study the phase stability of the dispersoidal liquids. The levels of soap/fatty acid concentration is varied. See Table 9.

TABLE 9

EXAMPLES 25-28
Soap Concentration Series
(No Stabilizing Ingredients)

| Ingredients | 25 Wt. % | 26 Wt. % | 27 Wt. % | 28 Wt. % |
|---|---|---|---|---|
| % Soap | 9.35 | 10.2 | 11.05 | 11.9 |
| % FFA | 6.27 | 6.84 | 7.41 | 7.98 |
| Soap/FFA Ratio | 1:0.67 | 1:0.67 | 1:0.67 | 1:0.67 |
| Accelerated Stability | Fail | Fail | Fail | Fail |
| Initial Viscosity | 23,000 | 38,000 | 50,000 | 55,000 |
| Cycle Viscosity | 110,000 | 145,000 | 155,000 | 155,000 |

Examples 25-28 without stabilizer at room temp. are all phase stable liquid dispersoidal with acceptable initial viscosities; but all fail the accelerated stability test which is conducted under above stress conditions. See Method III above for details.

TABLE 10

EXAMPLES 29-31
The effect of Fatty Acid Chain Length Distribution
% Soap = 10.2
% FFA = 6.84
These formulas also contained the stabilizing
ingredients (0.2% Xanthan, 0.5% KCl, 0.5% PGE)

| Ingredients | 29 Wt. % | 30 Wt. % | 31 Wt. % |
|---|---|---|---|
| % $C_{12}$ of Total FA's Mix | 13.5 | 100 | — |
| % $C_{14}$ of Total FA's Mix | 33.5 | — | — |
| % $C_{16}$ of Total FA's Mix | 24 | — | — |
| % $C_{18}$ of Total FA's Mix | 29 | — | 100 |
| Accelerated Stability | Pass | Pass | Pass |
| Initial Viscosity | 28,000 | 15,200 | 4,000 |
| Cycle Viscosity | 79,200 | 740,000 | 17,200 |
| Hand Lather | Good | Fair | Very Poor |
| Titer Point °C. | 59.5 | 44.2 | 69.6 |

Examples 29-31 are formulated the same as Example 2, but for their fatty acid chains. The preferred soap chain mix is used in Example 29. They all pass the accelerated stability test. A mix containing some higher fatty acid chains and titers about 59.5° C. is preferred for cycle stability. Note that Examples 29 and 26 are the same but for 29 has stabilizers which provides stability for its cycle viscosity and accelerated stability.

TABLE 11

EXAMPLES 32-34
The Effect of Fatty Acid Chain Length Distribution
% Soap = 10.2
% FFA = 6.84
These formulas also contained the stabilizing
ingredients (0.2% Xanthan, 0.5% KCl, 0.5% PGE)

| Ingredients | 32 Wt. % | 33 Wt. % | 34 Wt. % |
|---|---|---|---|
| % $C_{12}$ of Total FA's Mix | 50 | 62.5 | 12.5 |
| % $C_{14}$ of Total FA's Mix | — | 12.5 | 12.5 |
| % $C_{16}$ of Total FA's Mix | — | 12.5 | 12.5 |
| % $C_{18}$ of Total FA's Mix | 50 | 12.5 | 62.5 |
| Accelerated Stability | Pass | Pass | Pass |
| Initial Viscosity | 3,200 | 13,000 | 4,400 |
| Cycle Viscosity | 336,000 | 210,000 | 66,800 |
| Hand Lather | Fair | Moderate | Poor |
| Titer Point °C. | 56.9 | 50.9 | 63.7 |

Examples 32-34 are the same as Example 2, but for the soap chains. They all pass the accelerated stability test. The mixes with higher chains and titers of about 59.5° C. or above are preferred for cycle stability.

The initial viscosities of Examples 32 and 34 can be increased with the use of more thickener and salt in the formulation.

Referring to Table 12 below, these additional liquid soaps are made using the same formula but with I. V.'s of 11, 8, and 5 and with titers of 54.8, 55.9 and 57.4 respectively; they all pass accelerated stability and have initial and cycle viscosities of 24,000 and 53,000; 5,200 and 60,800; and 3,200 and 36,000 respectively.

TABLE 12

EXAMPLES 35-38
The Effect of Saturation
% Soap = 10.2
% FFA = 6.84
Examples 35-38 also contain: 0.50% PGE, 0.5% KCl,
and 0.2% Xanthan

| Ingredients | 35 Wt. % | 36 Wt. % | 37 Wt. % | 38 Wt. % |
|---|---|---|---|---|
| Iodine Value | <1.0 | 14 | 20 | 30 |
| Accelerated Stability | Pass | Pass | Pass | Pass |
| Initial Viscosity | 28,000 | 29,800 | 57,600 | 13,000 |
| Cycle Viscosity | 79,000 | 175,000 | 105,000 | 26,000 |
| Hand Lather | Good | Very Poor | Very Poor | Poor |

The most preferred Iodine Values are below 1 for stability and lather reasons. An additional benefit of low Iodine Values is no production of rancid odors due to the oxidation of the unsaturated double bond.

TABLE 13

EXAMPLES 39-41
The Effect of Thickeners
% Soap = 10.2
% FFA = 6.84
Soap/FFA Ratio = 1:0.67

| Ingredients | 39 Wt. % | 40 Wt. % | 41 Wt. % |
|---|---|---|---|
| Thickener Type: | Acrysol | Hydroxy Ethyl Cellulose | Xanthan |
| Finished Product Level | 0.80% | 0.80% | 0.20% |
| Accelerated Stability | Slight | Slight | Fail |
| Initial Viscosity | 58,000 | 48,000 | 30,000 |
| Cycle Viscosity | 140,000 | 200,000 | 160,000 |

Table 13 supports:
(1) Thickeners improve the stability of the formula.
(2) Thickeners by themselves (without electrolyte) appear not to help the cycle viscosity stability.

TABLE 14

EXAMPLES 42-44
The Effect of Nonionic (Polyglycerol Esters)
% Soap = 10.2
% FFA = 6.84
Soap/FFA Ratio = 1:0.67
Formulas also contained: 0.50% KCl and 0.2% Xanthan

| Ingredients | 42 Wt. % | 43 Wt. % | 44 Wt. % |
|---|---|---|---|
| Nonionic Type | Caprol ET | Caprol 10G-4-0 | Capmul 8210 |
| Finished Product Level | 0.50% | 0.50% | 0.50% |
| Accelerated Stability | Pass | Pass | Pass |
| Initial Viscosity | 22,000 | 26,000 | 22,000 |
| Cycle Viscosity | 49,000 | 31,000 | 260,000 |

Caprol ET—mixed polyglycerol esters (HLB = 2.5, chain lengths $C_{12}$, $C_{14}$, $C_{16}$, $C_{18}$, 6-10 glycerol units; M.W. = 2300).
Caprol 10G-4-0—decaglycerol tetraoleate (HLB = 6.2; M.W. = 1800).
Capmul 8210—mono/diglycerides of caprylic/capric acids (HLB = 5.5-6.0; M.W. = 250).

Table 14 supports:

(1) Nonionics which have larger molecular weight (over about 1000) improve the cycle viscosity in the presence of electrolyte.

| Example | Shear Thinning Factors | | Shear Thinning Factor |
|---|---|---|---|
| | Viscosity (cps) at 1 sec$^{-1}$ | Viscosity (cps) at 10 sec$^{-1}$ | |
| 1B | 38,036 | 4,003 | 9.5 |
| A | 12,800 | 2,495 | 5 |
| B | 7,450 | 5,522 | 1.35 |
| C | 4,220 | 4,734 | 0.89 |
| D | 2,680 | 3,533 | 0.76 |

Examples A, B, C, and D are commercially available liquid personal cleansers, all packaged in pressure actuated pump containers. "A" is DOVE ® Beauty Wash which claims to be a "non-soap" product. "B" is LIQUID IVORY ® Soap, which is a K soap based product. "C" is Jergens Liquid Soap and is a synthetic surfactant based product. "D" is Liquid Dial. Example 1B has a very high viscosity at a shear rate of 1 sec$^{-1}$, but its high shear thinning factor (9.5.) makes it possible to pump easily out of a pressure actuated pump. Examples B, C, and D have low shear thinning factors and, therefore, their viscosities are low to ensure pumpability.

Example 1B of the present invention is three times as viscous as DOVE ® Beauty Wash and has a shear thinning factor about twice that of DOVE ® Beauty Wash. A viscous product with a high shear factor is highly desirable for both pumpability and in use properties.

What is claimed is:

1. A dispersoidal liquid soap personal cleansing composition comprising:
   A. from about 5% to about 20% by weight of potassium fatty acid soap;
   B. from about 2.5% to about 18% $C_8$-$C_{22}$ free fatty acid; wherein said fatty acid has an Iodine Value of from zero to about 15; and a titer of from about 44° to about 70° C.;
   C. from about 55% to about 90% water; and
wherein said soap and said free fatty acid have a weight ratio of about 1:0.5 to about 1:1; and wherein said product has a viscosity of from about 4,000 cps to about 100,000 cps; and wherein said composition contains no more than 10% synthetic surfactant by weight of said composition.

2. A liquid cleansing composition of claim 1 wherein said Iodine Value is less than 5 and said titer is from about 50 to about 70.

3. A liquid cleansing composition of claim 1 wherein said Iodine Value is less than 3 and said titer is from about 59 to about 70.

4. A liquid cleansing composition according to claim 1 comprising from about 6% to about 14% by weight of said potassium soap and from about 4% to about 9% by weight of said free fatty acid.

5. A liquid cleansing composition according to claim 1 comprising from about 1% to about 10% of a high lathering synthetic surfactant.

6. A liquid cleansing composition according to claim 1 wherein the ratio of potassium soap to free fatty acid is from about 1:0.6 to about 1:0.8; and wherein said fatty acid is highly saturated and has an Iodine Value of from zero to about 10; and wherein said fatty acid is composed of alkyl chain lengths ranging from $C_8$ to $C_{22}$; and wherein said fatty acid has a titer of from about 59 to about 70, and wherein said composition contains from about 2% to about 6% of a higher lathering synthetic surfactant; and wherein said product has a viscosity of from about 10,000 cps to about 80,000 cps.

7. A liquid cleansing composition according to claim 6 wherein said fatty acid has an Iodine Value from zero to 3 and wherein said synthetic surfactant is sodium lauroyl sarcosinate.

8. A liquid cleansing composition according to claim 1 wherein said composition has a shear thinning factor of at least 1.5 up to about 25.

9. A liquid cleansing composition according to claim 8 wherein said factor is from about 2 to about 20.

10. A liquid cleansing composition according to claim 8 wherein said shear thinning factor is from about 3 to about 15.

11. A liquid cleansing composition according to claim 1 wherein said fatty acid is composed of chain lengths ranging from $C_{12}$ to $C_{18}$.

12. A liquid cleansing composition according to claim 1 wherein said composition contains from about 60% to about 80% water; from about 6% to about 14% said potassium fatty acid soap; from about 4% to about 9% said free fatty acid; and wherein said fatty acid has an Iodine Value of from zero to 3 and wherein said viscosity is from about 20,000 cps to about 40,000 cps.

* * * * *